Figure 1:
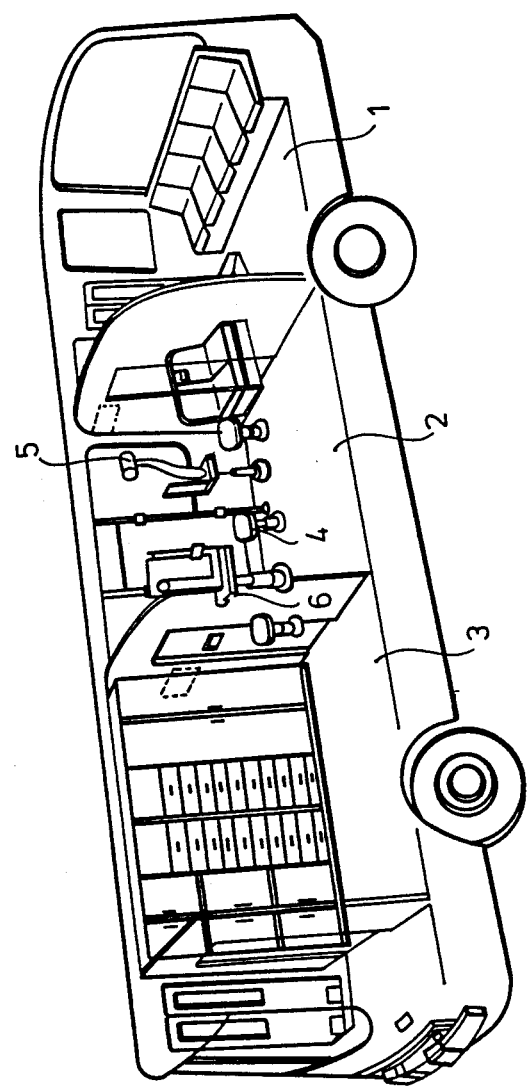

United States Patent [19]

János et al.

[11] Patent Number: 4,712,822
[45] Date of Patent: Dec. 15, 1987

[54] SIGHT-TESTING AMBULANCE BUS

[75] Inventors: Antal János, Budapest; Pojbics Jenö, Esztergom Rozetti, both of Hungary

[73] Assignee: Latszereszeti Eszkozok Gyara, Hungary

[21] Appl. No.: 857,856

[22] Filed: Apr. 30, 1986

[30] Foreign Application Priority Data

May 3, 1985 [HU] Hungary ............................ 1695/85

[51] Int. Cl.⁴ ............................................. B60P 3/14
[52] U.S. Cl. .................................. 296/24 R; 248/649; 248/677; 248/352
[58] Field of Search ................... 296/24 R, 1 F, 178; 351/244, 245; 248/649, 677, 354.1 (U.S. only), 352; 280/763.1

[56] References Cited

U.S. PATENT DOCUMENTS

| | | | |
|---|---|---|---|
| 1,625,075 | 4/1927 | Clement et al. | 351/245 |
| 1,664,517 | 4/1928 | Liebl | 296/24 R |
| 2,817,846 | 12/1957 | Stift | 296/24 R |
| 3,694,023 | 9/1972 | Burgess | 296/24 R |
| 4,055,206 | 10/1977 | Griffin | 296/24 R |
| 4,139,280 | 2/1979 | Kohler | 351/245 |

FOREIGN PATENT DOCUMENTS 3000037  7/1981  Fed. Rep. of Germany ...... 296/178

Primary Examiner—Robert B. Reeves
Assistant Examiner—Carol L. Olson
Attorney, Agent, or Firm—Handal & Morofsky

[57] ABSTRACT

A sight-testing ambulance bus for performing ophthalmologic examinations and providing appropriate spectacles expediently in rural areas, in which the instruments being sensitive against mechanical vibration of the chassis of the bus excited by movement in the bus are supported independently from the bus by support rods extended through holes in the bus-floor and standing on the ground under the bus. The support rods are fixed on the bus floor when the bus is moving and shock-absorbers protecting the instruments from vibrations when the bus is driven.

4 Claims, 5 Drawing Figures

SIGHT-TESTING AMBULANCE BUS

The invention relates to a sight-testing ambulance bus which has an inner space including at least a sight-testing room and an optical workshop, the sight-testing room is equipped with instruments required for performing ophtalmological examinations and the optical workshop is equipped with tools such as grinders and control instruments required for manufacturing spectacles.

It is well known in the art that there is a standing national demand for providing high-level medical care in rural areas like smaller villages, scattered rural settlements or the like. Such demands are generally satisfied by using mobile medical care facilities which are often built in buses or other vans. The Hungarian company Ikarus has already produced a number of special buses intended for offering ambulance care in several clinical fields. A bus has already been publicly shown which was intended for sight-testing purposes and this bus included a waiting room, a sight-testing room and an optical workshop. In the practice, however, this bus has not obtained commercial acceptance, since the performance of sensitive ophthalmological examinations and of delicate glass-processing manufacturing methods have been largely disturbed by inevitable mechanical vibrations and swinging movements present in the mechanically suspended chassis of the bus. When the bus was parking, the movement of patients therein generated mechanical vibrations which rendered the performance of sensitive optical measurements and medical tests impossible.

It would be an obvious way of mechanically stabilizing a bus by using independent support legs to hold the whole weight of the chassis like in case of caravan cars or sleeping vans. Such outer supporting means can not provide a sufficient attenutation against vibrations, since the chassis of a bus is a long and resilient mechanical structure, and if there is a larger distance between the supporting legs, the resilient chassis is excited for vibration by people moving in the bus. To provide a fully rigid chassis and a vibration-free support would render the bus construction much more expensive than those buses which are manufactured in larger scales. Such a high price would render the sale of sight-testing buses impossible.

In addition to the problem connected with the mechanical vibrations caused by the movements of the people in a parking bus there is a further problem which is connected with the protection of sensitive instruments and tools against mechanical vibration effects which take place when the bus is moving. Such instruments are transported generally in vibration-protective packing and in many cases in disassembled condition. The portable use of such instruments in an ambulance bus renders their special packing or disassembly impractical and often impossible.

The object of the invention is to overcome the drawbacks described hereinabove and to provide a technical solution by which the inevitable mechanical vibrations of the chassis can not affect the operation of the sensitive instruments and which can provide an effective protection against vibration when the bus is moving.

In the following part of the description the term "instrument" is intended to cover all kind of medical examination device, optical machine, gauge and checking device usable in ophthalmology and in the manufacture of spectacles which can be harmfully influenced by unwanted mechanical vibrations.

These objects have been met by providing a sight-testing ambulance bus comprising an inner space including at least a sight-testing room and an optical workshop, the sight-testing room is equipped with instruments required for performing ophthalmological examinations and the optical workshop is equipped with tools and control instruments required for manufacturing spectacles and according to the invention the ones of said instruments which are sensitive against vibrations are mounted on a support plate supported by support rods with telescopically adjustable lengths and which can stand on the floor of the bus, the floor defines respective openings under the support rods which openings can be releasably covered or uncovered, and in a parking position of the bus when it is used as a sight-testing site, the rods are extending through these openings and they are standing on the ground under the bus, and a spacing is defined between the rods and any part of the bus or object fixed to the bus and this spacing is larger than the amplitude of vibration of this part or object that can take place during normal use, whereby the vibrating part or object can not touch the rod through the spacing.

In a preferable embodiment the support rod comprises tubes slidably inserted in one-another and the tubes define through-bores for receiving a fixing bolt, and the opening is covered by a cover plate which is pivotally fixed to the bus floor and it can be turned to cover or uncover the opening.

For decreasing the damaging effects of vibrations when the bus is moved the vibration-sensitive instruments are mounted on an intermediate plate which is supported from all directions through a shock-absorbing means, and it is also preferred if the intermediate plate can be rigidly fixed to the support plate to fix the intermediate plate during use.

Figure 2:
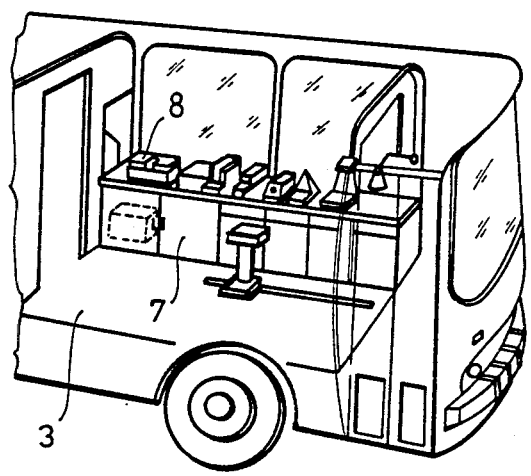
Figure 3:
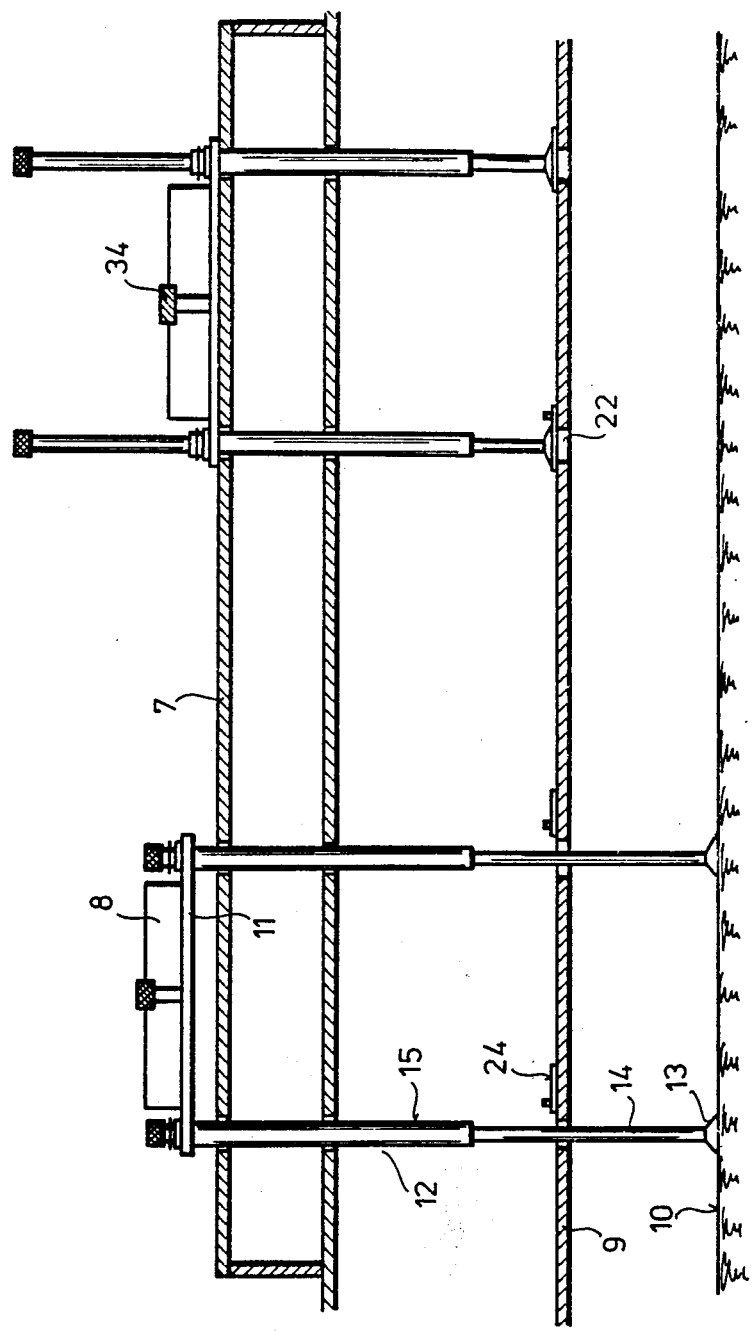
Figure 4:
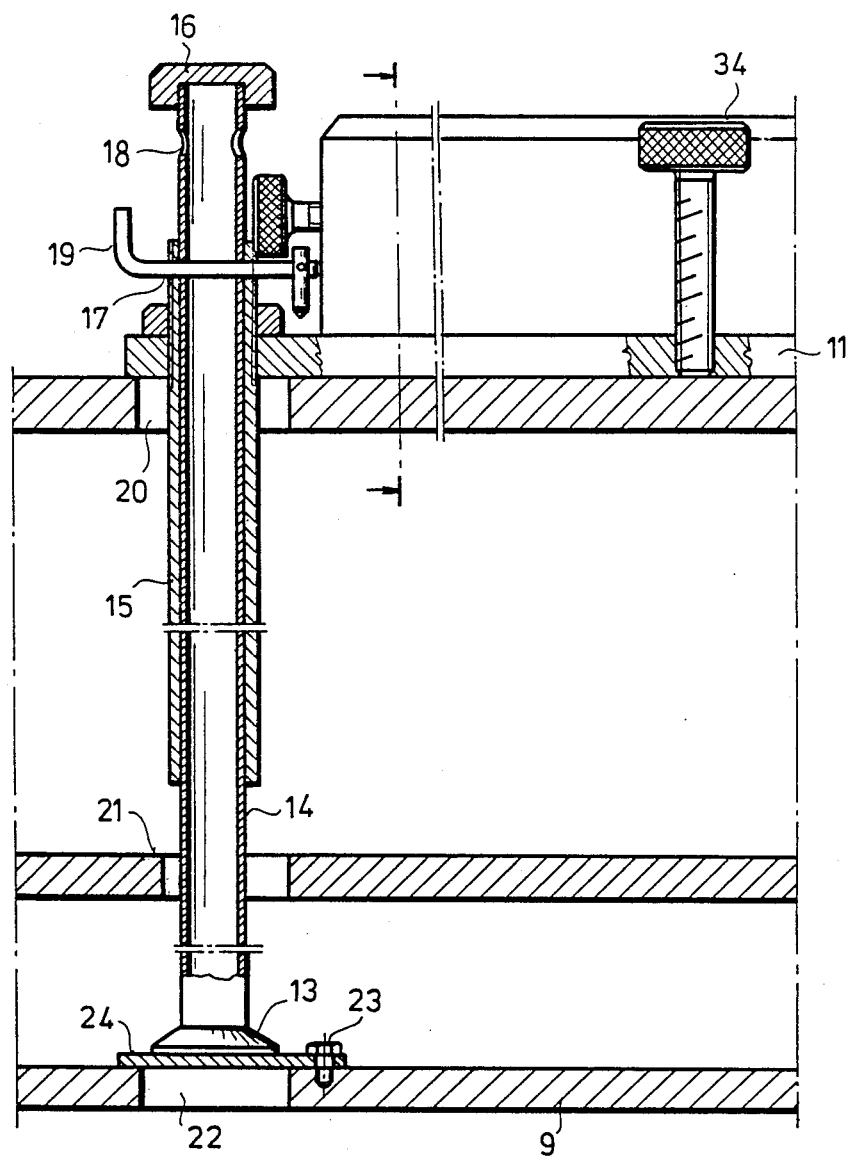
Figure 5:
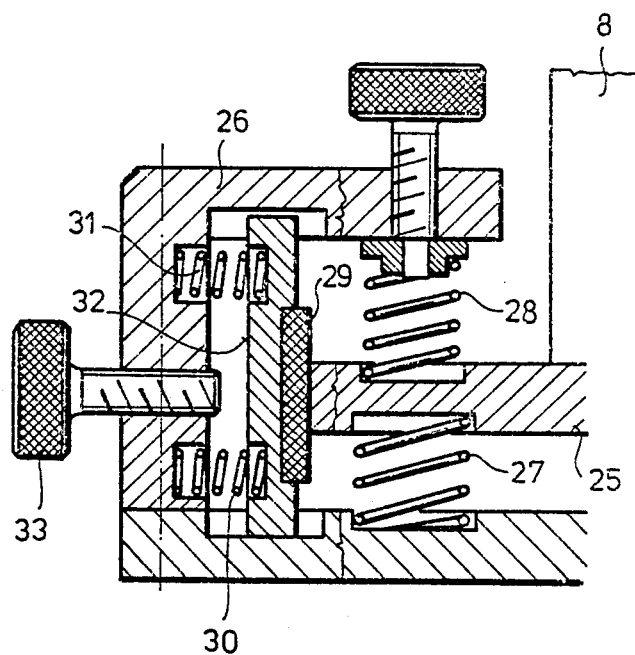

The invention will now be described in connection with a preferable embodiment thereof, in which reference will be made to the accompanying drawings. In the drawing:

FIG. 1 shows the general interior of the sight-testing bus in perspective view,

FIG. 2 is a perspective view similar to FIG. 1 showing the opposite side of the optical workshop relative to what is shown in FIG. 1, FIG. 3 shows an instrument mounted on a support plate during parking and moving state of the bus, respectively, FIG. 4 is an enlarged sectional elevation view showing the construction of the instrument support, and FIG. 5 is an enlarged sectional detail taken along line V—V of FIG. 4.

FIG. 1 shows an ambulance bus for sight-testing and ophthalmic examinations which has an inner space divided into three parts such as waiting room 1, ophthalmic examination room 2 and optical workshop 3 separated by respective transversal partition walls each provided with a door.

The waiting room 1 offers a sitting place for about five patients and this room serves as an entrance into the bus. In the examination room 2 there are examination chairs 4 and various ophthalmic and sight-testing instruments. These instruments comprise a gap-lamp 5 equipped with a tonometer and a Javal-type ophthalmometer 6. In the other side of the examination room 2 not shown in the drawing there can be arranged projector and a screen opposite therewith as well as a table extending by the wall and equipped with several drawers.

FIG. 2 shows the portion of the optical workshop 3 which is opposite to the one shown in FIG. 1, wherein working table 7 is extending through this portion and on the top of the working table 7 tools used for making spectacles and optical measuring and auxiliary instruments are arranged. Of the various means on the top of the working table instrument 8 used for grinding and optically measuring glasses for spectacles is excessively sensitive against mechanical vibrations. In the opposite side of the optical workshop 3 a large storage wardrobe is arranged which comprises a large number of drawers for receiving a stock of various glasses and frames.

By using the sight-testing ambulance bus a continuous patient care set up can be realized, since patients can proceed from the waiting room 1 to the examination room 2 for sight-testing and following the ophthalmic examination they can proceed to the optical workshop 3 where they can choose a suitable frame and the appropriate glasses will be made or selected and finally fitted in the frame, whereafter they can leave the bus in the frontal zone well-served and equipped with the appropriate spectacles.

The holding of those instruments and devices which are sensitive against mechanical vibrations is illustrated in FIGS. 3 to 5. FIG. 3 shows the working table 7, the instrument 8 thereon, floor 9 of the bus and ground surface 10 under the floor 9. The left side of FIG. 3 shows the instrument 8 in operational position, while on the right side of this figure the instrument 8 is shown in transport position. The instrument 8 is associated with a separate support plate 11 held by four support rods 12 arranged in the four corner regions thereof. Each support rod 12 comprises tube 14 provided with disc 13, an outer tube 15 receiving the tube 14 and handle 16 (see FIG. 4). The tube 14 can be moved telescopically in the interior of the outer tube 15 and comprises a number of through bores 17 and 18 made at appropriate heights. The outer tube 15 is also provided with a through bore above the support plate 11, and bolt 19 can be inserted through this bore and a selected one of the through bores of the tube 14, whereby the relative position of the tubes 14 and 15 and thus the height of the support plate 11 can be fixed. The outer tube 15 is fixed to the support plate 11 by a threaded joint (see FIG. 4). Large holes 20 and 21 made in upper and lower plates of the working table 11 enable on the one hand the releasable attachment of the tube 15 to the support plate 11 and on the other hand the free lifting and lowering of the tube 14. The floor 9 comprises opening 22 having a centre point falling in the vertical interconnection line of the centres of the holes 20 and 21 and this opening is releasable by cover plate 24 fixed pivotally to threaded bolt 23. In the left side of FIG. 3 the cover plate 24 is turned into open position and the tube 14 is extending through the opening 22 under the chassis of the bus and the disc 13 is supported on the ground surface 10. The support plate 11 is standing freely above the working table 7. The size of the holes 20, 21 and of the opening 22 is sufficiently large to provide enough spacing to prevent the tube 14 when being supported on the ground from being touched even if the bus is vibrated by the walking or other movement of the persons in the bus.

In the right side of FIG. 3 the support rod 12 stands on the cover plate 24 which closes now the opening 22 and it is supported by the bus floor 9. In this position the support plate 11 of the instrument 8 is lying on the working table 7. In this position the instrument 8 can be transported.

In order to prevent the instrument 8 from being damaged by mechanical vibration occuring when the bus is moving, a shock absorber shown in FIG. 5 is arranged between the instrument 8 and the support plate 11. The casing of the instrument 8 is mounted on intermediate plate 25 supported both from above and from below by respective coil springs 27, 28 abutting an inwardly bent rim 26 and the support plate 11, respectively. The rim 26 is rigidly fixed to the plate 11 or forming an integral part therewith. A disc member 29 made of a high friction material such as used for brake linings in motor vehicles is biased to the side of the intermediate plate 25 and a pressing element 32 pushed by springs 30, 31 is abutting the member 29. Between the element 32 and the rim 26 and between the element 26 and the support plate 11 there is provided a tolerance-gap which allows the free displacement of the element 32 along the direction of the biasing force of the springs 30, 31. A threaded bolt 33 can be adjusted from outward to engage the pressing element 32, by which the position of the mechanically attenuated swinging assembly can be fixed. For the sake of perfect and firm fixing of the position of this assembly a threaded pressing bolt 43 is used to press the instrument 8 to the support plate 11 from vertical direction.

The instrument supporting assembly described hereinabove can be used in the sight-testing bus for mounting all vibration-sensitive devices including the gap-lamp 5, the ophthalmometer 6 and the instrument 8. In the parking position of the bus the tubes 14 of the support rods 12 are extended to rest on the ground i.e. to stand independently from the suspension of the bus, and the respective device such as the instrument 8 is rigidly clamped by the above arrangement to the support plate 11. By such kind of support the instrument 8 will be made intact from any vibration of the bus-floor 9, therefore the inevitable oscillations, vibrations of the bus generated by the movement of the people in the bus can not affect or disturb the delicate optical examinations and working processes such as the grinding of the glasses or the instrumental measurements. When the bus is moving, the tubes 14 are standing on the floor 9, the support plate 11 is lying on the working table 7 and the instrument 8 is caught by the shock-absorbed intermediate plate 25, thus an additional mechanical protection has been provided against force effects that take place when the bus is moving.

In this way the invention has eliminated most of the obstacles which used to prevent the normal operation and use of the widely needed sight-testing ambulance bus.

We claim:

1. Sight-testing ambulance bus, comprising an inner space including at least a sight-testing room and an optical workshop, said sight-testing room being equipped with vibration sensitive instruments required for performing ophtalmological procedures, said optical workshop being equipped with tools and control instruments required for manufacturing spectacles, at least one of said instruments which is sensitive against vibrations is mounted on a respective support plate (11) supported by support rods (12) having telescopically adjustable lengths and standing on a floor (9) of said bus, said floor (9) defining respective openings (22) under said rods (12) being releasably covered and uncovered, and in a parking position of said bus said rods (12) extending through said openings (22) and abutting the ground under said bus, and a spacing (20,21,22) is formed between said rods (12) and the openings of said spacing being larger than the amplitude of vibration of a part of the bus that takes place during use, whereby said part can not touch said rod through said spacing.

2. The ambulance bus as claimed in claim 1, characterized in that said support rods (12) comprises a pair of tubes (14,15) slidably arranged in one-another, said tubes (14,15) extending through a plurality of bores (20,21) formed with said spacing around each of said tubes for receiving a positioning bolt (19), and one of said tubes (22) defined in said floor (9) is covered by a pivotally turntable cover plate (24).

3. The ambulance bus as claimed in claim 1, characterized in that said vibration sensitive instruments (8) are fixed on an intermediate plate (25), a resilient and mechanically attenuated coupling member coupling said intermediate plate to said support plate (11).

4. The ambulance bus as claimed in claim 3, characterized by further comprising releasable clamping means for rigidly coupling said intermediate plate (25) to said support plate (11) in said parking position.

* * * * *